US006547539B2

(12) United States Patent
Izraelev

(10) Patent No.: US 6,547,539 B2
(45) Date of Patent: Apr. 15, 2003

(54) PUMP ASSEMBLY WITH BEARING AND SEAL-FREE REUSABLE IMPELLER FOR FRAGILE AND AGGRESSIVE FLUIDS

(75) Inventor: Valentin M. Izraelev, Eden Prairie, MN (US)

(73) Assignee: Advanced Bionics, Inc., Hopkins, MN (US)

(*) Notice: Subject to any disclaimer, the term of this patent is extended or adjusted under 35 U.S.C. 154(b) by 24 days.

(21) Appl. No.: 09/862,123

(22) Filed: May 21, 2001

(65) Prior Publication Data

US 2002/0172608 A1 Nov. 21, 2002

(51) Int. Cl.$^7$ ............................. F04B 17/00; F03B 13/00
(52) U.S. Cl. ............................ 417/423.1; 417/423.14; 415/900
(58) Field of Search ...................... 417/423.1, 423.14, 417/420, 424.1, 423.7; 415/900

(56) References Cited

U.S. PATENT DOCUMENTS

| | | | |
|---|---|---|---|
| 5,360,317 A | * | 11/1994 | Clausen et al. ............ 415/900 |
| 5,685,700 A | | 11/1997 | Izraelev |
| 5,924,848 A | | 7/1999 | Izraelev |
| 5,938,412 A | | 8/1999 | Izraelev |
| 6,206,659 B1 | | 3/2001 | Izraelev |

* cited by examiner

Primary Examiner—Charles G. Freay
Assistant Examiner—Michael K. Gray
(74) Attorney, Agent, or Firm—Haugen Law Firm PLLP

(57) ABSTRACT

A pump for transferring fragile and aggressive fluids such as human blood, the pump comprising a housing with a sealed annular wall of uniform thickness forming a pumping chamber. The chamber is provided with inlet and outlet ports with a rotor being housed within the chamber coaxially of the housing. The housing includes opposed end cap portions with a cylindrical body portion interposed therebetween. The body portion includes first and second cylindrical segments with mating side walls adapted to be coupled together along an annular bonding seam, the arrangement providing for separation along the bonding seam to permit removal and reworking of the rotor for replacement in a fresh housing.

4 Claims, 4 Drawing Sheets

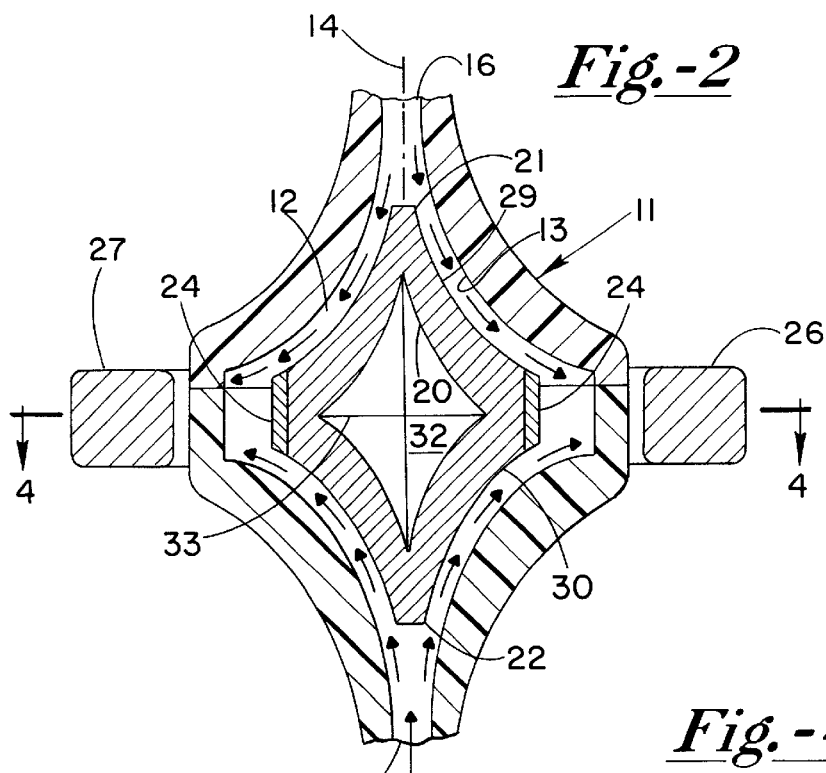
*Fig.-2*
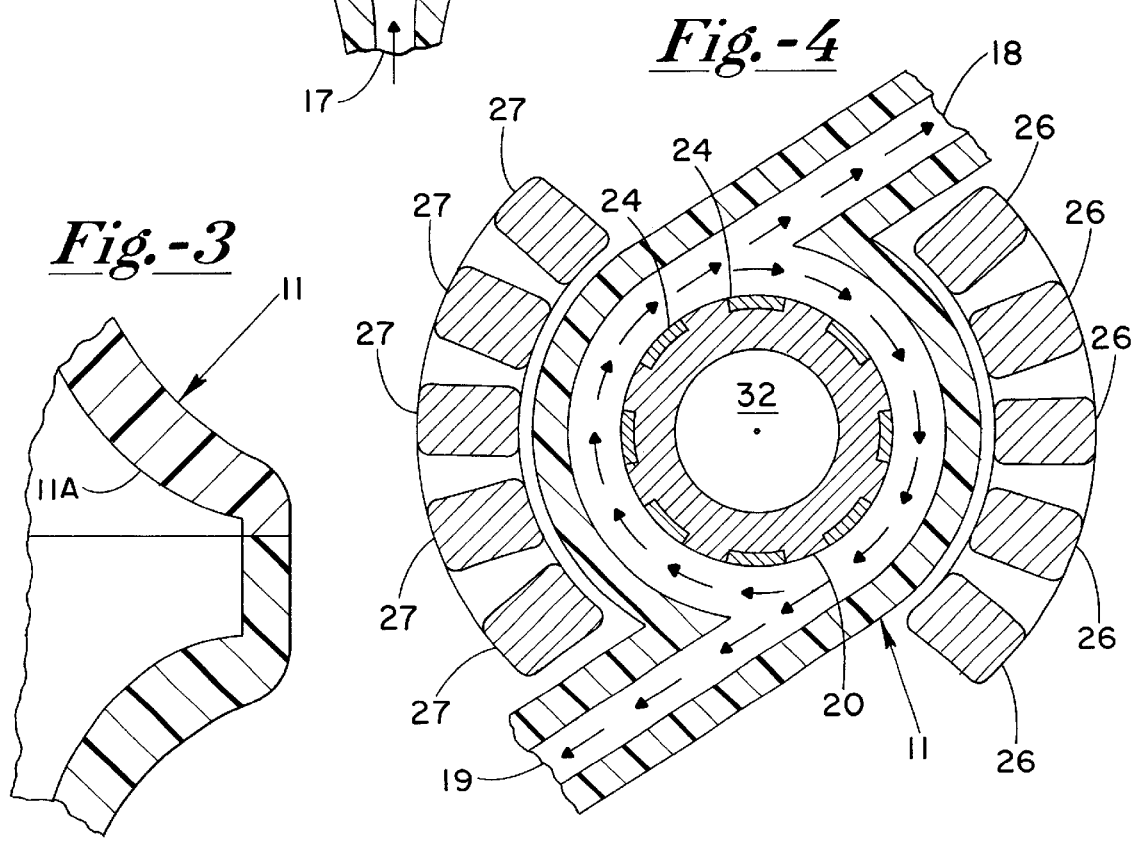
*Fig.-3*
*Fig.-4*

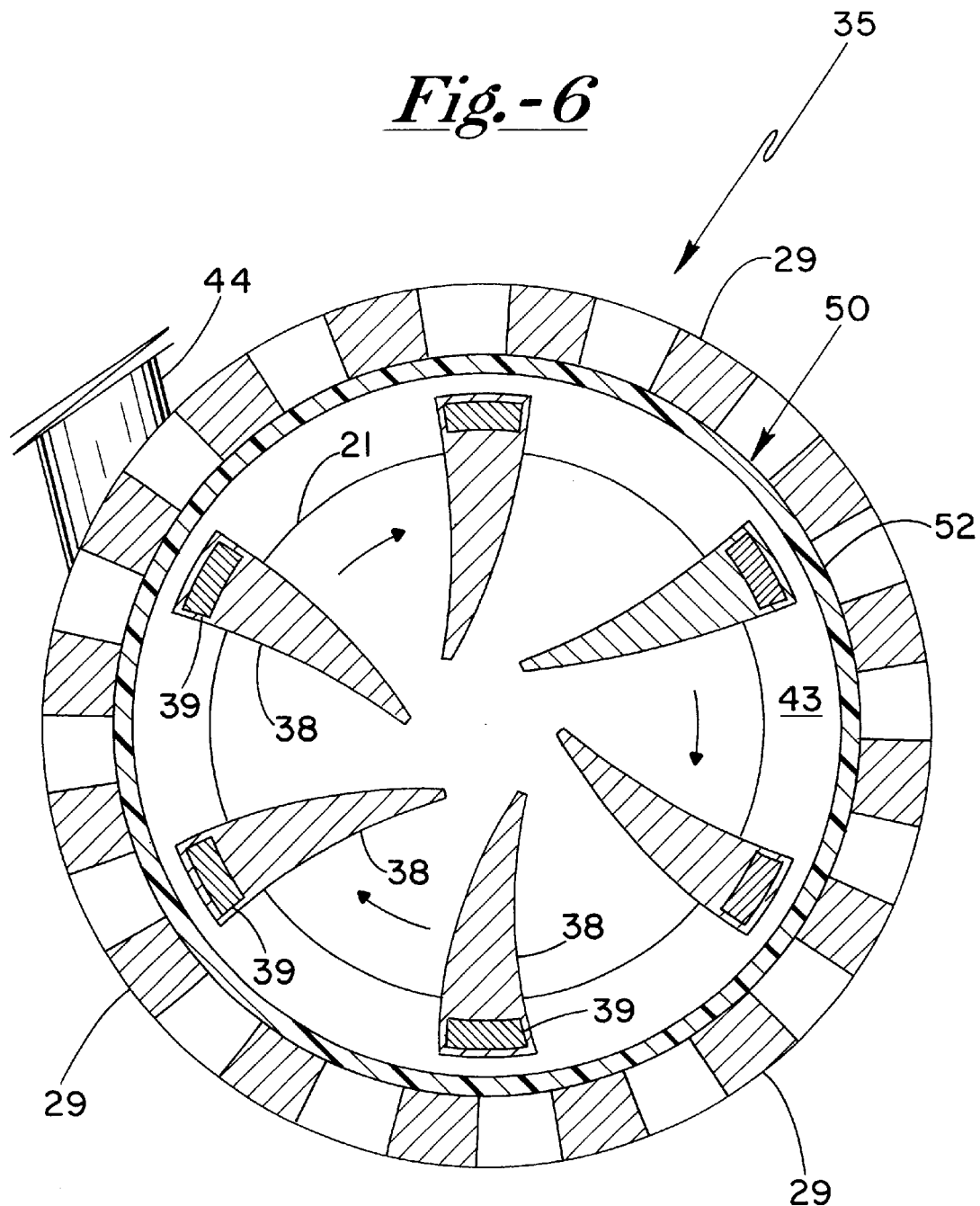

PUMP ASSEMBLY WITH BEARING AND SEAL-FREE REUSABLE IMPELLER FOR FRAGILE AND AGGRESSIVE FLUIDS

BACKGROUND OF THE INVENTION

The present invention relates generally to an improved pump for transferring fragile or aggressive fluids, and more particularly to a pump comprising a housing enclosing an impeller, and wherein the housing component is disposable, and with the impeller component being designed for reuse. The present invention is a modification of the pumps disclosed and claimed in my U.S. Pat. Nos. 5,685,700, 5,924, 848, 5,938,412, and 6,206,659, and each of which is assigned to the assignee of the present invention.

The pump structures of the present invention are designed to be bearing and seal-free, and with hydrodynamic forces supporting the impeller during operation. As such, these pumps are particularly well adapted for applications dealing with fragile fluids, including human or animal blood. Neither of these can tolerate exposure to forces such as unusual impact and/or sheer forces, and thus the advantages of utilizing bearing and seal-free pumps become apparent. Aggressive fluids include corrosive or poisonous fluids, as well as fluids which cannot tolerate contamination, or which otherwise may destroy seals and/or bearings to reduce the lifetime and/or longevity of the pump structure. Poisonous fluids, for example, are extremely dangerous when a leak develops, a common consequence of bearing failure. The pump of the present invention utilizes an impeller which is bearing and seal-free, being dynamically balanced during operation by a combination of hydrodynamic and buoyant forces. The pump of the present invention is particularly adapted for transferring human blood and is capable of creating a flow of such liquids without damaging and/or otherwise significantly adversely affecting the quality of the pumped fluid. Inasmuch as the impeller or rotor is reusable, it is economically sound practice to fabricate this component of materials which may either be costly, or alternatively, of materials which may present problems in fabrication due to their physical, chemical, and/or mechanical properties. Metals such as titanium and non-metals such as pyrolytic carbon and certain engineered plastics are examples of such materials.

Another feature of the impeller or rotor is that it be capable of receiving and reliably retaining electromagnetic components used in the drive system and capable of withstanding the cleaning operations, with such an array of permanent magnets being readily disposed within the rotor in a brushless motor configuration. Alternatively, permanent magnet-to-permanent magnet couplings may be employed and mounted in a similar fashion. Thus, the arrangement of the present invention provides for the economic utilization of a rotor which may be costly to fabricate initially, but because of its versatility and reusability, these rotors become highly economically viable.

In a typical application, any given assembly of the pump of the present invention and its associated structure is designed for single use only. In pumps of the present invention, following any given single use or application, the housing is separated into two or more parts, thereby freeing the rotor for subsequent cleaning and sterilization operations. Following the completion of the cleaning and sterilization operations, the rotor may be installed in a fresh housing. Housings of the present invention are provided with mating circumferential surfaces which are well adapted to be sealed together by means of adhesive and/or fusion bonding. The design of the pump of the present invention is such that housing tolerances are loose enough to provide for ease of assembly, with wide interchangeability of rotors being, of course, accommodated. Ease of reassembly is enhanced by virtue of the fact that the impeller or rotor is not attached physically to the housing.

SUMMARY OF THE INVENTION

In accordance with the present invention, a bearing and seal-free pump is provided comprising a housing which forms an operative enclosure about a hydrodynamically stable impeller or rotor. Means are provided for imparting rotational motion to the impeller, which is accordingly positioned within the chamber within the housing. Appropriate inlet and outlet ports are provided for accomplishing transfer of the fluid through the pump structure.

Therefore, it is a primary object of the present invention to provide an improved bearing and seal-free pump comprising a housing forming an enclosed pumping chamber in which a rotor is disposed. Being bearing and seal-free, relatively wide manufacturing tolerances may be accommodated, with the housing and rotor components being fabricated of appropriately selected materials. Inasmuch as the rotor is designed to be reusable, a wider variety of materials may be included in the list of suitable materials.

It is yet a further object of the present invention to provide an improved bearing and seal-free pump structure which has a configuration designed for ease of assembly and disassembly, thereby enhancing the utility of the system.

Other and further objects of the present invention will become apparent to those skilled in the art upon a study of the following specification, appended claims, and accompanying drawings.

IN THE DRAWINGS

FIG. 2 is a vertical sectional view taken through the axis of the structure as illustrated in FIG. 1, and illustrating the flow pattern created by the pump when in actual operation;

FIG. 3 is a detail fragmentary view of that portion of the housing which is adapted for sealing following introduction of the rotor into the pump chamber;

FIG. 4 is a horizontal sectional view of the pump structure illustrated in FIG. 1, and showing the detail of the flow pattern of the pump during operation;

FIG. 6 is a horizontal sectional view of the pump structure illustrated in FIG. 5, and being taken along the line and in the direction of the arrows 6—6 of FIG. 5.

DESCRIPTION OF THE PREFERRED EMBODIMENT

Figure 1:
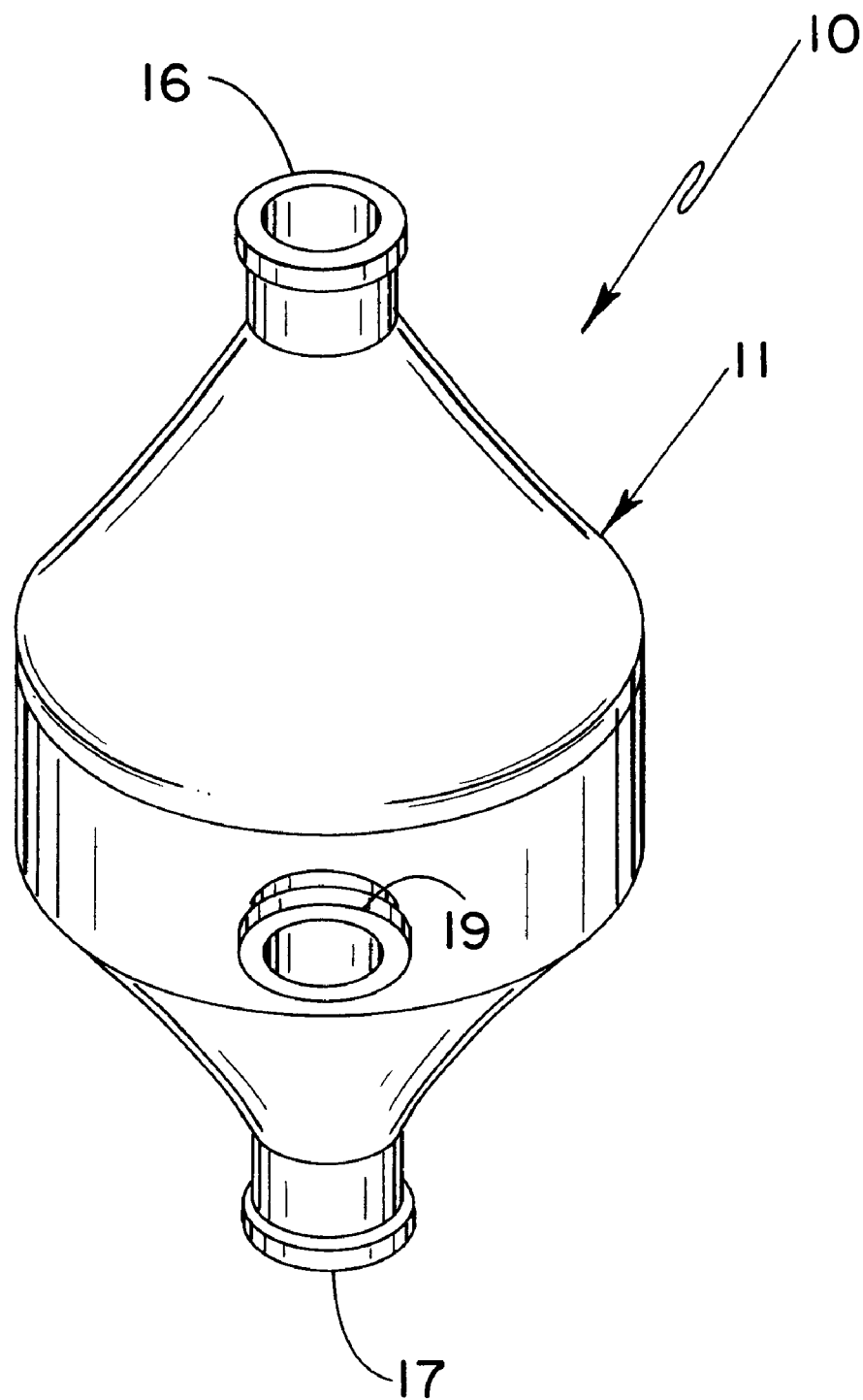
FIG. 1 is a perspective view of the exterior of a pump assembly prepared in accordance with the present invention.

In accordance with the preferred embodiment of the present invention, and with particular attention being directed to FIGS. 1, 2 and 4 of the drawings, the pump generally designated 10 comprises a housing 11, the interior of which defines pumping chamber 12. As will be discussed in detail hereinafter, housing 11 comprises a pair of mating components sealed together about the annular wall portions defining the perimeter. By separating the housing 11, the rotor may be removed, cleaned and sterilized, and installed in a fresh housing.

The inner periphery 13 of housing 11 forms the outer periphery of the chamber 12. As is clear from the views of FIGS. 2 and 4, housing 11 and chamber 12 share a central axis which extends along axis 14 as set forth in FIG. 2. Housing 11, and accordingly chamber 12, is provided with a pair of inlet ports as at 16 and 17, along with outlet ports as at 18 and 19. Inlet ports 16 and 17, collectively, define the inlets to the chamber, while outlet ports 18 and 19 collectively define the outlets. The inlet ports 16 and 17 are arranged coaxially with the chamber, that is, along axis 14, with the inlet ports being arranged in oppositely disposed relationship to chamber 12. Outlet ports 18 and 19 are arranged medially of the inlet ports, and are, as indicated, disposed generally transversely of axis 14.

With continued attention being directed to FIGS. 2 and 4 of the drawings, rotor 20 is disposed within chamber 12 and has a symmetrical dual conical configuration. This configuration provides dual cones converging toward opposed polar regions such as 21 and 22, and the rotor is provided with an axis of rotation which extends between the polar regions 21 and 22. The base of each of the two cones forming the dual cone configuration are coupled together and form a common center plane. This common center is further utilized as a mounting base for a plurality of permanent magnets such as magnets 24—24. These magnets are arranged at radially spaced locations generally medially along the axis of rotation of rotor 20, with the permanent magnets being provided at equally radially and arcuately spaced locations. Electromagnetic drive means are provided as at 26—26 and 27—27, with the electromagnetic drive means being, in turn, coupled to a source of electrical energy and arranged to deliver rotational driving energy to the rotor through the permanent magnets 24—24. The drive arrangement is, of course, commonly referred to as a brushless motor configuration and brushless motor drives are, of course, well known in the art. The rate of rotation of rotor 20 is conveniently controlled by means of the frequency of the field applied to electromagnetic members 26-26 and 27-27, with the rate of rotation being controlled by the frequency of the applied electromagnetic field, or by selective energization of the electromagnetic means 26—26 and 27—27. Such drives are, of course, commonly utilized and well known in the art.

Figure 5:
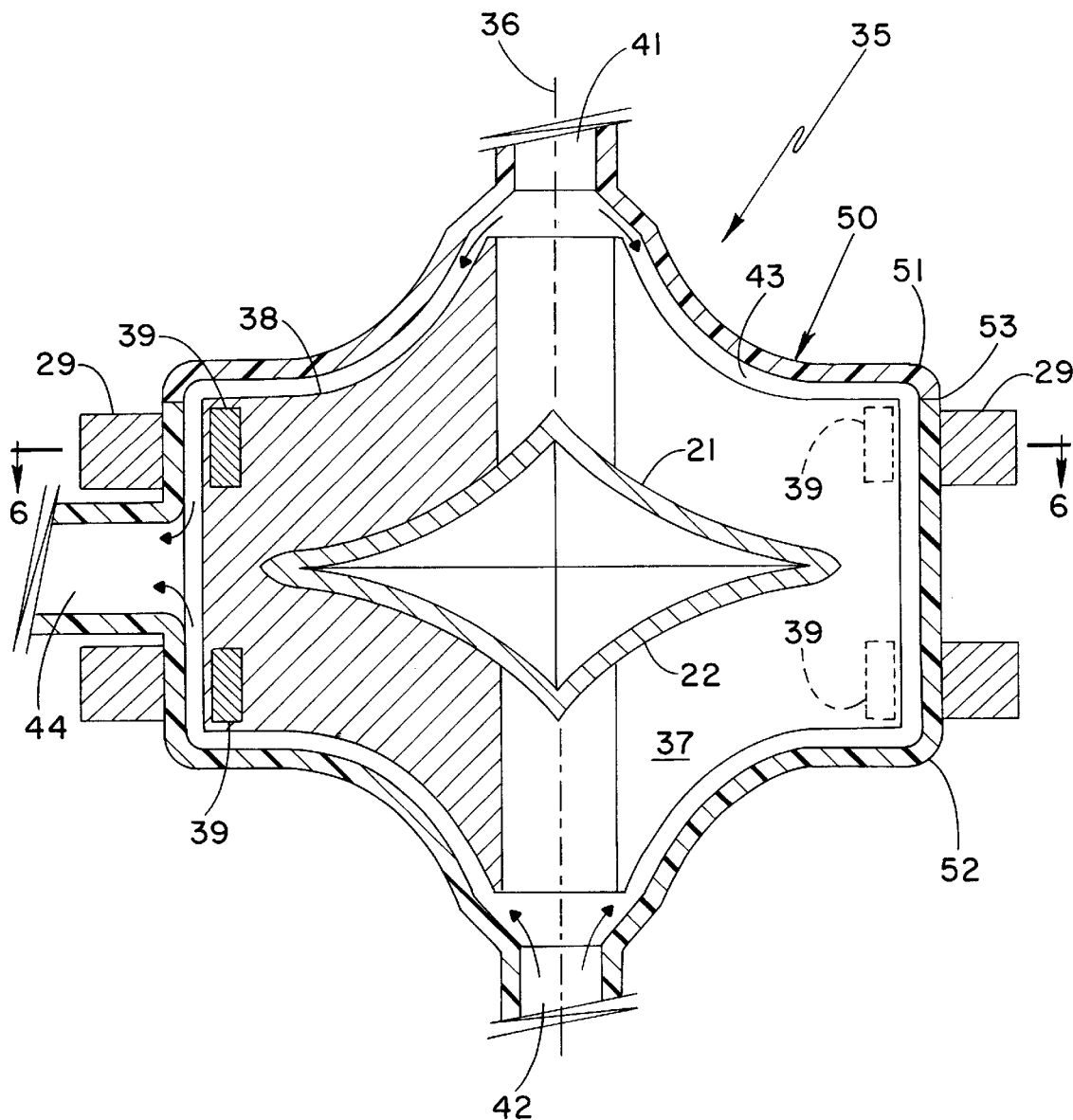
FIG. 5 is a vertical sectional view taken through the axis of a modified form of pump, and illustrating the flow pattern created during actual operation.

In the pump assembly of FIGS. 5 and 6, the pump 35 includes a pumping chamber with a central axis 36, and with a rotor body 37 being disposed within the chamber for bearing and seal-free rotation therewithin. The pump structure of FIG. 5 is disclosed and claimed in U.S. Pat. No. 5,924,848 referred to hereinabove. The rotor 37 has a double or dual-conical configuration which converges toward opposed polar regions, and with the axis of rotation extending between these polar regions. Rotor 37 is further provided with radial vanes 38—38 extending radially outwardly relative to the axis of rotation. These vanes are utilized to enhance flow, as well as to provide a zone for encapsulation of magnetic drive components 39—39. Magnetic drive components 39 are typically arranged symmetrically in axially spaced apart relationship relative to the transverse axis of the rotor. Fluid inlet ports 41 and 42, are arranged in the pumping chamber in oppositely disposed relationship within the chamber 43, with the fluid being transported or transferred to the inlet port area either externally or internally of the chamber. Except for those occasions when the rotor is displaced, it is normally arranged in coaxial relationship with both the pumping chamber and the fluid inlet ports. The outlet port or ports 44 are arranged generally medially of the chamber, midway between the inlet ports and typically are positioned tangentially of the medial portion of the pumping chamber. In those situations where the axis of rotation of the rotor is arranged along a vertical axis, the dual-conical configuration is such that flow on the outside portion of the rotor proceeds downwardly on the upper portion, and upwardly on the lower portion of the dual-cone rotor. See arrows indicating flow.

THE HOUSING

Housing generally designated 50 comprises two segments including segment 51 and segment 52. These segments are joined and bonded together at seal 53. Seal 53 is utilized to bond the segments 51 and 52 together, and may be undertaken by conventional secure bonding techniques. Examples of suitable techniques include fusion bonding as well as bonding with highly durable and acceptable adhesives. Such secure bonding techniques including the use of suitable adhesives are known to those of skill in the art.

When a pump assembly has been utilized for a particular application, and need for sterility is required before a subsequent use, housing or shell 50 is separated at the seal zone 53, or other suitable location. When separated, rotor or impeller 37 is removed and separately subjected to a sterilization operation such as thermally or through exposure to a sterilizing atmosphere such as ethylene oxide or the like, the sterilization following, of course, a thorough cleansing operation. Thereafter, impeller 37 is reintroduced into a fresh housing or shell 50 including fresh segments 51 and 52, whereupon the bonding operation is undertaken to render the assembly fully useful.

With respect to the areas of the inlet and outlet ports, it is generally preferred that the combined area of the inlet ports be generally equal to the combined areas of the outlet ports, thereby providing more consistency in flow and pressures, and also providing for an appropriate hydrodynamic balancing of the rotor 20 within the chamber 12.

Rotor 20 is further defined by walls 29 and 30, with the preferred material of construction being titanium. A suitable biocompatible material such as pyrolytic carbon, polycarbonate, acrylic, or copolymers of polystyrene may also be employed. Alternatively, a coating may be applied to a suitable substrate in order to enhance the biocompatibility of the structure, with pyrolytic carbon being one highly suited coating. In those instances where the device is not being employed for implantation, but nevertheless is intended for incidental contact with human blood, then, of course, other materials may be employed, provided that the blood-contacting surfaces be formed and/or coated with a non-thrombogenic material.

THE ROTOR DETAIL

Rotor 20 is provided with a hollow core or void area as at 32, with this area providing a means for controlling the relative density of the rotor body. Preferably, the relative density is selected by the ratio of the relative density of the rotor to that of the fluid being pumped, and in most applications, the relative density of the rotor to the fluid being pumped is between about 0.3 and 0.6, with it being understood that relative densities of between about 0.1 and 0.9 may be found useful. Also, the dual conical configuration of rotor 20 provides the finished structure with an axial length along the axis of rotation as being generally equal to the axial length of the pumping chamber between the inlet ports 16 and 17. The transverse diameter of the rotor 20 is defined along a medial plane, as along medial line 33 and with the configuration of the dual converging cones providing a clearance between the surface of the rotor and the inner surface of the pumping chamber as illustrated in greater detail in FIG. 5. The rate of increase of clearance is preferably proportional to the increase of the circumference of the rotor from the polar tip to the medial plane, with this increase in clearance providing a generally consistent rate of motion for the fluid being pumped as it moves along its translational and rotational motions and/or vectors. With these considerations in mind and for pumping human blood, the clearance between the inner surface of the pumping chamber and the periphery of the rotor preferably ranges from between about 1 millimeter up to about 7 millimeters, with a narrower range of between about 1 millimeter and 3 millimeters being generally preferred. Generally, a clearance of about 1.5 millimeters is preferred.

While the rotor structure illustrated is described as being relatively smooth, vanes may be employed on the structure with the vanes forming arcuately spaced passages within the rotor. In other words, the vanes may be formed as individual arcuately spaced paddles to form spaced-apart fluid passages and/or channels. One such structure is illustrated in FIGS. 5 and 6.

The moment of inertia of the rotor or impeller is effectively minimized by virtue of the positioning of the mass of the impeller closer to the center of gravity (or center of mass). This may be obtained by moving the mass of the impeller needed for structural integrity closer to the center, and generally as closely as possible to the rotational axis. The moment of inertia may be controllably adjusted in connection with the structure of the present invention by arranging and mounting the permanent magnets within a circular or annular zone which is at the maximum radius of the rotor inner impeller, as required, while increasing the strength of the structure along its axis of rotation.

GENERAL COMMENTARY

As has been indicated, the drive means for the electromagnetic drive elements 26—26 and 27—27 is preferably in the form of conductor windings, and for purposes of achieving appropriate hydrodynamic balance, the windings are carefully controlled and selectively made so as to preserve the hydrodynamic balance of the rotating rotor while eliminating the need for any form of bearing.

With respect to the fluid being pumped, it should be noted that the human blood has a viscosity of about 4 centipoises at 25° C., and this viscosity is sufficient to provide for sufficient friction between a relatively smooth rotor surface and blood so as to achieve a sufficient rotational component of motion for hydrodynamic balancing. As the rotational velocity of the fluid being pumped increases, its hydrodynamic balance effect will, of course, increase correspondingly and proportionately. With a rotational velocity of approximately 1000 rpm, the hydrodynamic balancing effect substantially overwhelms the buoyant effect afforded by the relative density of the rotor within the chamber.

For start-up purposes, saline is normally preferred as the functional material, with the saline being employed for a period of time until the desired rotational velocity is achieved, and thereafter blood may be introduced as the working solution being pumped and/or transferred.

An example of an external transfer of fluids between the oppositely disposed fluid inlet ports is a fluid transfer line which introduces the fluids at opposite ends of the housing. As an example of an internal transfer, a bore may be provided which extends between opposite ends of the rotor, thereby permitting transfer of fluids internally of the structure.

The term "oppositely disposed inlet ports" is intended to reflect the utilization of fluid introduction at opposite ends of the rotor, and is also intended to include those arrangements wherein all of the fluid being pumped is initially introduced into one polar region of the housing, with the fluid nevertheless being transferred either internally or externally of the housing directly to the oppositely disposed polar region.

The pump shown in the drawings is in operational mode with the rotor spinning about its axis of rotation and with all forces acting on the rotor balanced. In the stationary/non-operational mode with the fluid in the housing, only the buoyant forces are acting on the rotor, and the rotor floats up in the random position. In the stationary/non-operational mode with no fluid in the housing, the rotor is resting on the interior of the housing under gravitational forces.

Levitation of the rotor, as indicated, is achieved by a combination of hydrodynamic and buoyant forces. Briefly, the buoyant component is achieved as a result of careful selection of the rotor density, with the preferred relative density being between about 0.1 and 0.9 of the relative density of the fluid being pumped. In a dynamic and operational mode, the buoyant forces merely become a component of lesser or secondary importance to the more significant and more highly effective hydrodynamic force.

The hydrodynamic force component is achieved as a result of the motion of the fluid as it is being moved through the pumping chamber. As the velocity of the fluid increases, the hydrodynamic forces increase substantially, and with the proper selection of rotor density, the hydrodynamic forces which are created during normal operation result in achieving a precise, steady and controllably repeatable centering of the rotor within the pumping chamber.

The overall dimensions of the pump assembly prepared in accordance with the present invention will be determined primarily with the individual application. Those of conventional skill in the art will, of course, be able to relate the appropriate dimensional configuration given the requirements and demands of the specific application.

It will be appreciated, of course, that various modifications may be made in the preferred embodiment illustrated above, and these modifications may be made without actually departing from the spirit and scope of the present invention.

What is claimed is:

1. A pump for transferring fluids especially fragile and aggressive fluids such as human blood and comprising a housing having inner and outer peripheral surfaces with a sealed annular wall of uniform thickness therebetween, and with said inner peripheral surface defining a pumping chamber with a central axis, a rotor disposed within said pumping chamber, inputting means arranged in polar relationship to said pumping chamber and coaxially with said pumping chamber during operational rotation of said rotor, an outputting means arranged transversely and generally medially of said inlet port means, said rotor having a dual conical configuration converging toward opposed polar regions and having an axis of rotation extending between said polar regions and arranged coaxially with the axis of said pumping chamber, magnetic driving means arranged on said rotor at radially spaced locations generally medially along said axis of rotation, electromagnetic drive means coupled to a source of energy and arranged to deliver rotational driving energy to said rotor through said magnetic driving means, said pump being further characterized in that:

(a) the housing forming said pumping chamber having a central portion of regular cylindrical configuration and with opposed conical end cap portions, said central portion comprising first and second cylindrical segments having end walls bonded together along mutually opposed abuttingly mated planar annular end surfaces to form a uniform annular seam, each of said planar annular end surfaces being disposed along a plane perpendicular to said pumping chamber axis, with said annular bonding seam being uniform and defining a continuum along said mated annular end surfaces of each of said first and second uniform annular segments, the arrangement being such that said bonding seam may be broken to separate said first and second cylindrical segments so as to permit cleaning, sterilization, and introduction of said rotor for sealed recycling into a fresh annular housing.

2. The pump of claim 1 wherein said rotor has a relative density substantially less than that of the fluid being pumped and within a range of between 10% and 90% of the density of the fluid being pumped.

3. The pump of claim 1 wherein said bonding seam is formed through fusion bonding.

4. The pump of claim 1 being particularly characterized in that said bonding seam is formed of an adhesive compatible with human blood.

* * * * *